(12) United States Patent
Riegel et al.

(10) Patent No.: US 7,553,903 B2
(45) Date of Patent: *Jun. 30, 2009

(54) SWELLABLE HYDROGEL-FORMING POLYMERS HAVING A LOW FRACTION OF FINES

(75) Inventors: Ulrich Riegel, Landstuhl (DE); Thomas Daniel, Waldsee (DE); Matthias Weismantel, Jossgrund-Oberndorf (DE); Mark Elliott, Ludwigshafen (DE); Dieter Hermeling, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 423 days.

This patent is subject to a terminal disclaimer.

(21) Appl. No.: 10/581,562

(22) PCT Filed: Dec. 17, 2004

(86) PCT No.: PCT/EP2004/014396

§ 371 (c)(1),
(2), (4) Date: Jun. 2, 2006

(87) PCT Pub. No.: WO2005/061014

PCT Pub. Date: Jul. 7, 2005

(65) Prior Publication Data

US 2007/0106239 A1    May 10, 2007

(30) Foreign Application Priority Data

Dec. 19, 2003 (DE) ................. 103 60 394
Feb. 3, 2004 (DE) ..................... 10 2004 005 417

(51) Int. Cl.
*C08G 63/60* (2006.01)
*C08G 69/26* (2006.01)

(52) U.S. Cl. ................. 524/599; 524/606; 524/916

(58) Field of Classification Search ................. 524/916, 524/599; 604/367
See application file for complete search history.

(56) References Cited

U.S. PATENT DOCUMENTS

| | | | | |
|---|---|---|---|---|
| 4,061,684 A | * | 12/1977 | Helfert et al. ................. 568/613 |
| 4,417,992 A | * | 11/1983 | Bhattacharyya et al. .... 252/88.1 |
| 5,275,838 A | | 1/1994 | Merrill |
| 5,346,986 A | | 9/1994 | Schneider et al. |
| 5,560,929 A | * | 10/1996 | Hedstrand et al. ........... 424/486 |
| 5,562,646 A | * | 10/1996 | Goldman et al. ............. 604/368 |
| 5,589,256 A | | 12/1996 | Hansen et al. |
| 5,641,561 A | | 6/1997 | Hansen et al. |
| 5,681,878 A | | 10/1997 | Klotzsche et al. |
| 5,684,107 A | | 11/1997 | Schneider et al. |
| 5,714,166 A | * | 2/1998 | Tomalia et al. ............... 424/486 |
| 5,731,365 A | * | 3/1998 | Engelhardt et al. ........... 523/206 |
| 5,786,429 A | * | 7/1998 | Allen ........................ 525/430 |
| 5,840,321 A | | 11/1998 | Engelhardt et al. |
| 5,919,442 A | * | 7/1999 | Yin et al. ................. 424/78.18 |
| 5,938,934 A | * | 8/1999 | Balogh et al. ................ 210/688 |
| 5,994,440 A | * | 11/1999 | Staples et al. ................ 524/377 |
| 6,414,214 B1 | * | 7/2002 | Engelhardt et al. ........... 604/368 |
| 6,565,768 B1 | * | 5/2003 | Dentler et al. ............... 252/194 |
| 6,784,267 B1 | * | 8/2004 | Ward et al. .................... 526/311 |
| 6,818,018 B1 | * | 11/2004 | Sawhney ................. 623/11.11 |
| 7,312,268 B2 | * | 12/2007 | Kim ........................... 524/403 |
| 2001/0020062 A1 | * | 9/2001 | Abuelyaman et al. ....... 524/600 |
| 2002/0082359 A1 | * | 6/2002 | Ramesh ...................... 525/437 |
| 2002/0165337 A1 | * | 11/2002 | Wallace et al. ............... 528/373 |
| 2002/0177828 A1 | * | 11/2002 | Batich et al. ................. 604/367 |
| 2003/0108917 A1 | * | 6/2003 | Huh et al. ........................ 435/6 |
| 2003/0134132 A1 | * | 7/2003 | Winterton et al. ........... 428/451 |
| 2003/0211072 A1 | * | 11/2003 | Carreno-Gomez et al. ........................ 424/78.17 |
| 2003/0224052 A1 | * | 12/2003 | Van Dyke ................... 424/484 |
| 2004/0044321 A1 | * | 3/2004 | Kainth et al. ................ 604/367 |
| 2005/0020734 A1 | * | 1/2005 | Asgarzadeh et al. ........ 523/400 |
| 2005/0084474 A1 | * | 4/2005 | Wu et al. .................... 424/76.1 |
| 2005/0215966 A1 | * | 9/2005 | Borgmann et al. .......... 604/368 |
| 2005/0222279 A1 | * | 10/2005 | Larsson et al. ................ 521/50 |
| 2007/0004903 A1 | * | 1/2007 | Hoff et al. ................... 528/480 |
| 2007/0066947 A1 | * | 3/2007 | Beck et al. .................. 604/368 |
| 2007/0244283 A1 | * | 10/2007 | Riegel et al. ................ 526/318 |

FOREIGN PATENT DOCUMENTS

| | | |
|---|---|---|
| EP | 0 679 678 | 11/1995 |
| EP | 0 755 964 | 1/1997 |
| WO | WO-92/13912 | 8/1992 |
| WO | WO-94/22940 | 10/1994 |
| WO | WO-03/20978 | 3/2003 |

OTHER PUBLICATIONS

Hult, Hyperbranched polymers, Enc. of Poly. Sci. and Tech., John Wiley and Sons, 2001.*
International Search Report in PCT/EP2004/014396 dated Apr. 22, 2005.

* cited by examiner

*Primary Examiner*—Mark Eashoo
*Assistant Examiner*—Liam J Heincer
(74) *Attorney, Agent, or Firm*—Marshall, Gerstein & Borun LLP

(57) ABSTRACT

Swellable hydrogel-forming polymer comprising at least one hydrophilic polymer of dendritic structure, a process for preparing the swellable hydrogel-forming polymer and also its use in hygiene articles.

19 Claims, No Drawings

SWELLABLE HYDROGEL-FORMING POLYMERS HAVING A LOW FRACTION OF FINES

CROSS-REFERENCE TO RELATED APPLICATIONS

This is the U.S. national phase application of International Application No. PCT/EP2004/014396, filed Dec. 17, 2004, which claims the benefit of German patent application No. 103 60 394.8, filed Dec. 19, 2003 and German patent application No. 102004005417.7, filed Feb. 3, 2004.

The present invention concerns swellable hydrogel-forming polymers having a low fraction of fines, a process for preparing swellable hydrogel-forming polymers having a low fraction of fines and also their use.

Swellable hydrogel-forming polymers, known as superabsorbent polymers (SAPs) or superabsorbents for short, are known from the prior art.

Swellable hydrogel-forming polymers are in particular polymers of (co)polymerized hydrophilic monomers, graft (co)polymers of one or more hydrophilic monomers on a suitable grafting base, crosslinked cellulose ethers, crosslinked starch ethers, crosslinked carboxymethylcellulose, partially crosslinked polyalkylene oxide or natural products which are capable of swelling in aqueous fluids, such as guar derivatives for example. Such hydrogels are used as products capable of absorbing aqueous solutions to manufacture diapers, tampons, sanitary napkins and other hygiene articles, but also as water-retaining agents in market gardening or to thicken all kinds of wastes, especially medical wastes.

Swellable hydrogel-forming polymers are preferably capable of absorbing at least 10 times their own weight and preferably 20 times their own weight, based on the polymer used, of 0.9% by weight sodium chloride solution. This absorption is preferably achieved even under a pressure of 0.7 psi for example.

Swellable hydrogel-forming polymers are typically surface or gel postcrosslinked to improve their performance characteristics. This postcrosslinking is known per se to one skilled in the art and preferably takes place in an aqueous gel phase or as surface postcrosslinking of the ground and classified polymeric particles.

Superabsorbents are subject to abrasive processes during production and processing and cause corners to be knocked off particles, which creates a fine dust, or fines. The fine dust produced leads to filter plugging, tacky deposits, clumping and appreciable problems with conveying the superabsorbent. The large surface area of the dust is responsible for rapid absorption of moisture from the surroundings and for precipitate dust to become sticky, which leads to contamination of manufacturing equipment. Furthermore, hard agglomerates of dust form within pneumatic conveying systems. Furthermore, the fine attritus is considered extremely undesirable by hygienists and occupational physicians.

Unless the fine dust is specifically separated off, it will lead to problems at superabsorbent production or before the polymer is incorporated in a hygiene article and also to much reduced saline flow conductivity (SFC) of the gel in use. This then leads to increased rates of leakage.

Processes for dedusting superabsorbents have therefore already been proposed in the patent applications WO-A-92/13912, WO-A-94/22940 and EP-A-0 679 678.

WO-A-92/13912 and WO-A-94/22940 describe the dedusting of superabsorbents by surfacial coating with polyethylene glycols. Polyethylene glycols are disadvantageous in that, being linear and water-soluble polymers, they greatly increase the viscosity of the solution surrounding the gel particles and so reduce the fluidity of the solution. Used in a hygiene article, this leads to inferior saline flow conductivity (SFC) in the swollen gel.

EP-A-0 679 678 describes a process wherein the dust content of a pulverulent superabsorbent is reduced by after treatment with silicones. This reference also recommends the use of additional dedusting agents, such as polyglycols and polyglycol ethers for example. Silicones have an undesirable hydrophobicizing effect on superabsorbents, which reduces their swell rate.

EP-A-0 755 964 describes the surface coating of superabsorbents with insoluble waxes. However, the waxes used have a hydrophobicizing effect on superabsorbents in some instances and are difficult to disperse without assistants. But the dispersants customarily used as assistants for these purposes have a surface-active character and lower the surface tension of the liquid entrapped in the hygiene article, and this can in turn lead to leakage.

U.S. Pat. No. 5,641,561 and U.S. Pat. No. 5,589,256 describe the use of suitable polymeric and non-polymeric binders in binding superabsorbent particles to fibers. The binder shall be capable of binding superabsorbent particles to the fibers in the hygiene article via hydrogen bonds. The possible adverse effect of the binder on the swollen gel's saline flow conductivity, especially with regard to the disclosed polymeric binders, or the surface tension of the liquid entrapped in the hygiene article is not mentioned, nor is any disclosure of a solution to these problems. Moreover, it must be emphasized with regard to the non-polymeric binders that these are not very desirable as solvents in hygiene articles because of their out-gassing in the use state and their effect on skin. There is no disclosure of teaching to minimize such solvents while at the same time dedusting and binding the particles to the fiber.

It is accordingly an object of the present invention to provide a process for preparing swellable hydrogel-forming polymers, known as superabsorbents, wherein a superabsorbent having a low fraction of fine dust is obtained and wherein neither the swellability nor the saline flow conductivity is made inferior compared with the untreated superabsorbent.

It is a further object of the present invention to provide a process for preparing swellable hydrogel-forming polymers wherein the fine dust content of the superabsorbent obtained increases only insignificantly, if at all, on exposure to a mechanical stressor. Fine dust refers to particles less than 10 μm in diameter.

It is a further object of the present invention to provide a process for preparing superabsorbents wherein the superabsorbents are aftertreated with powdery and/or dusty additives and wherein the superabsorbents have a low fraction of fine dust.

It is a further object of the present invention to provide a process for preparing superabsorbents wherein superabsorbents having an optimized behavior for conveyance are obtained. The superabsorbents obtained here shall exhibit a certain tackiness in order, for example, that they may be readily metered with conveyor screws without any increase in the tendency to cake, especially at high relative humidity.

We have found that these objects are achieved, surprisingly, by using hydrophilic polymers of dendritic structure in the preparation of swellable hydrogel-forming polymers superabsorbents having a low fraction of fine dust, especially after exposure to a mechanical stressor, an improved ability to bind to powdery and/or dusty additives, a high rate of swell, a high saline flow conductivity and optimal flow behavior.

Dendritic polymers are defined in Römpp, Lexikon-Chemie, Georg Thieme Verlag, Stuttgart, 10$^{th}$ edition, page 898, as synthetic macromolecules which are constructed by stepwise attachment of two or more monomers at a time to each previously attached monomer, so that the number of monomer end groups grows exponentially with every step to ultimately create a spherical treelike structure.

Hydrophilic polymers of dendritic structure which are useful for the purposes of the present invention are polyols having 8 or more, preferably 16 or more and more preferably 32 or more hydroxyl groups and a nonlinear skeleton which has preferably been branched 14-fold or more and more preferably 30-fold or more.

Hydrophilic polymers of dendritic structure include for example polyesters which are obtained from a polyol by esterification with a $C_3$-$C_{20}$-hydroxycarboxylic acid, preferably with a $C_4$-$C_{12}$-hydroxycarboxylic acid and more preferably with a $C_5$-$C_8$-hydroxycarboxylic acid, the hydroxycarboxylic acid comprising at least two hydroxyl groups, preferably two hydroxyl groups, and/or at least two carboxylic acid groups. Particular preference is given to hydroxycarboxyhlic acids having two hydroxyl groups and one carboxylic acid group, especially 2,2-dimethylolpropionic acid. Polyols are compounds having at least two hydroxyl groups, examples being ethylene glycol, diethylene glycol, triethylene glycol, polyethylene glycol, propylene glycol, dipropylene glycol, tripropylene glycol, polypropylene glycol, butylene glycol, 1,3-propanediol, 1,4-butanediol, bisphenol A, glycerol, trimethylolpropane, pentaerythritol and/or sorbitol. Preference is given to dendritic polyesters, with particular preference being given to Boltorn® 20, Boltorn® 30, Boltorn® 40 and Boltorn® 310 (Perstorp Specialty Chemicals AB, Sweden).

Useful hydrophilic polymers of dendritic structure for the purposes of the present invention further include polymers which are obtainable by condensation of polyols having at least three hydroxyl groups and subsequent alkoxylation. Examples thereof are branched polyethylene glycols obtainable by condensation of glycerol molecules and subsequent ethoxylation.

Useful hydrophilic polymers of dendritic structure for the purposes of the present invention further include all polymers which are obtainable by addition polymerization of a monomer having at least one hydroxyl group and subsequent alkoxylation. The addition polymerization is preferably carried out in the presence of a crosslinker. This gives polymer particles which have a hydrophilic surface because of a multiplicity of hydroxyl groups at the surface. For example, so-called star polyethylene glycols are obtainable according to Makromol. Chem. 189, 2885 (1988) by free-radical polymerization of p-hydroxyethylstyrene and subsequent alkoxylation.

Further examples of useful polymers according to the present invention are the highly branched polymers of the HYBRANE® brand and also the Astramol Dendrimers® (DSM N.V., NL). They include in particular highly branched poly(propyleneimine)s, obtainable for example from butylenediamine by repeated multiple Michael addition with acrylonitrile and hydrogenation, star polycaprolactones, star nylon-6, highly branched polyesteramides, for example on the basis of the addition product from succinic anhydride and diethanolamine in a molar ratio of 1:1. The process of the present invention can also be carried out using so-called PAMAM dendrimers based on poly(amidoamine), obtainable for example from ammonia by repeated multiple reaction with methyl acrylate and ethylenediamine.

It is possible to use polyglycerols, star-shaped polyethylene glycols and also other hydrophilic compounds, but preferably polyalcohols, of sphere- or cumulus-shaped, nonlinear molecular geometry.

Preference is given to such hydrophilic polymers of dendritic structures as have a glass transition temperature Tg from 20 to 100° C. and more preferably from 25 to 50° C. and/or an average molecular weight from 1000 to 10 000 g/mol and more preferably from 2000 to 6000 g/mol.

The amount of hydrophilic polymer of dendritic structure utilized in the process of the present invention is preferably in the range from 0.005% to 10% by weight, more preferably in the range from 0.01% to 5% by weight, even more preferably in the range from 0.05% to 1% by weight and especially in the range from 0.10% to 0.80% by weight, based on the swellable hydrogel-forming polymer.

The hydrophilic polymers of dendritic structure are preferably mixed with the dried water-absorbing hydrogel. Dry refers preferably to a water content of less than 20% by weight and more preferably of less than 10% by weight. But the hydrophilic polymer of dendritic structure can also be added to the swellable hydrogel-forming polymer before, during and/or after the surface-postcrosslinking operation, but it is preferably added during the surface-postcrosslinking operation.

The form of mixing is not subject to any restrictions, but preference is given to using reaction mixers or mixing and drying ranges, such as for example Lödige® mixers, BEPEX® mixers, NAUTA® mixers, SCHUGGI® mixers, NARA® dryers and PROCESSALL®. Fluidized bed dryers can also be used moreover. The mixing is advantageously carried out using a residence time from 1 to 180 minutes and preferably from 5 to 20 minutes and a speed from 25 to 375 rpm and preferably from 100 to 150 rpm.

When applied together with the surface-postcrosslinking solution, the surface postcrosslinker can be applied together with the dendritic polymer in solution; alternatively, separate streams of liquid can be jetted into the postcrosslinking mixer via separate nozzles. When additives in dust or powder form are applied, it is further possible to dissolve the dendritic polymer in a solvent in which the dusty or powdery additive can be dispersed as well. This mixture may optionally also include the surface postcrosslinker.

Useful solvents include all conventional solvents used in surface postcrosslinking. Particular preference is given to water and preference is further given to 1,2-propanediol, 1,3-propanediol, 1,4-butanediol, isopropanol, ethanol, methanol, ethylene carbonate, propylene carbonate, glycerol and also mixtures thereof. Particular preference is given to mixtures of water with one or more of the aforementioned organic solvents. However, the choice of solvent is governed by the requirements which lead to effective production of the solution and is not restricted to the aforementioned ones.

Optionally, one or more surface-active substances or dispersants may be added to the solvent. It is possible to add preferably nonionic surfactants such as for example sorbitan monolaurate (Span 20), sorbitan monododecanate, sorbitan monohexadecanate, sorbitan monooctadecanate, sorbitan monooleate, sorbitan sesquioleate, sorbitan trioleate which are obtainable under the tradenames Span 40, Span 60, Span 80, Span 83, Span 85.

Preferably, however, no surface-active substance is added to the solution as a dispersing aid.

The dendritic polymer's solution or dispersion, which may optionally include one or more dispersed dusty or powdery additives, which may optionally include a dispersing assistant, which may further optionally include aluminum sulfate or a soluble metal salt of some other 3- or 4-valent metal, and which optionally may include at least one surface post-crosslinker, is preferably prepared by melting (if necessary) the dendritic polymer and pouring the melt into the solvent or into a portion of the solvent and subsequently diluting with the other portion. The operation is preferably accompanied by thorough stirring and more preferably by turbulent stirring, using an Ultraturax for example. Alternatively, the dendritic polymer can also be melted directly in the hot solvent or in a portion thereof. Furthermore, the dendritic polymer can also be dispersed for example using ultrasound or else suitable nozzles.

When dusty or powdery additives are to be dispersed in as well, it is particularly advisable to use a suitable continuous or batch mixer to prepare the dispersion. Particular preference is given to mixers from IKA-Werke GmbH & Co KG which are designated MHD 2000/4, MHD 2000/5 and also CMS 2000/4. Mixers of similar construction and other makes as well can also be used, of course. It is further possible to use grinding pumps as described in DE 10131606, for example NEWX 80-50-315, from Wernert-Pumpen GmbH, to prepare the dispersion.

In specific cases, the dispersion can also be prepared by batch- or continuous-operated ultrasonication. It is further possible to use the customary conventional wet-grinding process to prepare the dispersion. Particular preference is also given to wet-chemical precipitation of fine particles by chemical reaction between soluble components with or without stirring while heating. This generally leads to particularly finely divided precipitates.

The present invention further provides swellable hydrogel-forming polymers which are obtainable by the process of the present invention, especially swellable hydrogel-forming polymers comprising less than 100 weight ppm, preferably less than 50 weight ppm and more preferably less than 10 weight ppm of particles less than 10 μm in diameter, and also their use for absorbing blood and/or body fluids, especially urine.

The present invention further provides swellable hydrogel-forming polymers which are obtainable by the process of the present invention, especially swellable hydrogel-forming polymers comprising less than 100 weight ppm, preferably less than 50 weight ppm and more preferably less than 10 weight ppm of particles less than 10 μm in diameter, wherein the swellable hydrogel-forming polymer comprises at least one powdery and/or dusty additive, such as for example metal salts, such as aluminum sulfate and/or magnesium sulfate, pyrogenic silicas, such as Aerosil®, polysaccharides and derivatives thereof, nonionic surfactants, waxes, diatomaceous earth and/or hollow microspheres, and also their use for absorbing blood and/or body fluids, especially urine.

Hollow microspheres are described in Chem. Ing. Techn. 75, 669 (2003). Hollow microspheres are gas-filled or evacuated globular solid particles from 1 to 1000 μm in diameter. Their wall thickness is typically between 1% and 10% of the diameter. Wall materials are not subject to any restriction. Possible wall materials are glass, ceramic-forming oxides or interoxides, silicates, aluminosilicates, polymers, polycondensates and metals.

The swellable hydrogel-forming polymers of the present invention typically have a saline flow conductivity (SFC) of at least $20 \times 10^{-7}$ cm$^3$s/g, preferably at least $40 \times 10^{-7}$ cm$^3$s/g, more preferably at least $60 \times 10^{-7}$ cm$^3$s/g, even more preferably at least $150 \times 10^{-7}$ cm$^3$s/g, and most preferably at least $300 \times 10^{-7}$ cm$^3$s/g. Very particular preference is also given to hydrogel-forming polymers having an SFC value of 500-$2000 \times 10^{-7}$ cm$^3$s/g which are obtained according to the present invention.

Powdery additives preferably have an average particle size of less than 2000 μm, more preferably less than 400 μm.

Dusty additives have an average particle size of less than 200 μm, preferably less than 50 μm and more preferably less than 10 μm.

The present invention further provides hygiene articles comprising superabsorbents prepared according to the present invention.

The swellable hydrogel-forming polymers which can be used in the process of the present invention are in particular polymers of crosslinked (co)polymerized hydrophilic monomers, polyaspartic acid, graft (co)polymers of one or more hydrophilic monomers on a suitable grafting base, crosslinked cellulose ethers, crosslinked starch ethers or natural products which are swellable in aqueous fluids, such as guar derivatives for example. Preferably, the polymer to be crosslinked is a polymer which comprises structure units which derive from acrylic acid or esters thereof or which were obtained by graft copolymerization of acrylic acid or acrylic esters on a water-soluble polymeric matrix. These hydrogels will be known to one skilled in the art and are described for example in U.S. Pat. No. 4,286,082, DE-C-27 06 135, U.S. Pat. No. 4,340,706, DE-C-37 13 601, DE-C-28 40 010, DE-A-43 44 548, DE-A-40 20 780, DE-A-40 15 085, DE-A-39 17 846, DE-A-38 07 289, DE-A-35 33 337, DE-A-35 03 458, DE-A-42 44 548, DE-A-42 19 607, DE-A-40 21 847, DE-A-38 31 261, DE-A-35 11 086, DE-A-31 18 172, DE-A-30 28 043, DE-A-44 18 881, EP-A-0 801 483, EP-A-0 455 985, EP-A-0 467 073, EP-A-0 312 952, EP-A-0 205 874, EP-A-0 499 774, DE-A-26 12 846, DE-A-40 20 780, EP-A-0 205 674, U.S. Pat. No. 5,145,906, EP-A-0 530 438, EP-A-0 670 073, U.S. Pat. No. 4,057,521, U.S. Pat. No. 4,062,817, U.S. Pat. No. 4,525,527, U.S. Pat. No. 4,295,987, U.S. Pat. No. 5,011,892, U.S. Pat. No. 4,076,663 or U.S. Pat. No. 4,931,497. The content of the above named patent documents as far as it concerns the type and preparation of these hydrogels is expressly part of the present publication.

Examples of hydrophilic monomers suitable for preparing these swellable hydrogel-forming polymers are acids which are capable of addition polymerization, such as acrylic acid, methacrylic acid, vinylsulfonic acid, vinylphosphonic acid, maleic acid, maleic anhydride, fumaric acid, itaconic acid, 2-acrylamido-2-methylpropanesulfonic acid, 2-acrylamido-2-methylpropanephosphonic acid and also their amides, hydroxyalkyl esters and amino- or ammonio-containing esters and amides and also the alkali metal and/or ammonium salts of the acid-functional monomers. It is further possible to use water-soluble N-vinylamides such as N-vinylformamide or else diallyldimethylammonium chloride. Preferred hydrophilic monomers are compounds of the general formula I

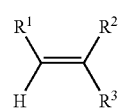

(I)

where
$R^1$ is hydrogen, $C_1$-$C_4$-alkyl, such as for example methyl or ethyl, or carboxyl, $R^2$ is —$COOR^4$, hydroxysulfonyl or phosphonyl, a phosphonyl group esterified with a $C_1$-$C_4$-alkanol, or a group of the formula II

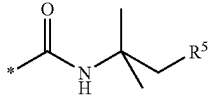

$R^3$ is hydrogen, $C_1$-$C_4$-alkyl, such as for example methyl or ethyl, $R^4$ is hydrogen, $C_1$-$C_4$-aminoalkyl, $C_1$-$C_4$-hydroxyalkyl, alkali metal ion or ammonium ion, and $R^5$ is a sulfonyl group, a phosphonyl group or a carboxyl group or a respective alkali metal or ammonium salt.

Examples of $C_1$-$C_4$-alkanols are methanol, ethanol, n-propanol, isopropanol or n-butanol.

Particularly preferred hydrophilic monomers are acrylic acid and methacrylic acid and also their alkali metal or ammonium salts, for example sodium acrylate, potassium acrylate or ammonium acrylate.

Suitable grafting bases for hydrophilic hydrogels which are obtainable by graft copolymerization of olefinically unsaturated acids or their alkali metal or ammonium salts can be of natural or synthetic origin. Examples are starch, cellulose or cellulose derivatives and also other polysaccharides and oligosaccharides, polyalkylene oxides, especially polyethylene oxides and polypropylene oxides, and also hydrophilic polyesters.

Suitable polyalkylene oxides have for example the formula III

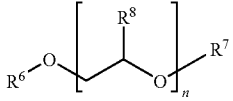

where $R^6$, $R^7$ are independently hydrogen, $C_1$-$C_{12}$-alkyl, such as for example methyl ethyl, n-propyl or isopropyl, $C_2$-$C_{12}$-alkenyl, such as for example ethenyl, n-propenyl or isopropenyl, $C_7$-$C_{20}$-aralkyl, such as for example phenylmethyl, 1-phenylethyl or 2-phenylethyl, or aryl, such as for example 2-methylphenyl, 4-methylphenyl or 4-ethylphenyl, $R^8$ is hydrogen or methyl, and n is an integer from 1 to 10 000.

$R^6$ and $R^7$ are each preferably hydrogen, $C_1$-$C_4$-alkyl, $C_2$-$C_6$-alkenyl or phenyl.

Preferred hydrogels are in particular polyacrylates, polymethacrylates and also the U.S. Pat. No. 4,931,497, U.S. Pat. No. 5,011,892 and U.S. Pat. No. 5,041,496 graft polymers.

The swellable hydrogel-forming polymers have preferably been crosslinked, i.e., they comprise compounds having at least two double bonds which have been polymerized. into the polymeric network. Suitable crosslinkers are in particular N,N'-methylenebisacrylamide and N,N'-methylenebismethacrylamide, esters of unsaturated mono- or polycarboxylic acids of polyols, such as diacrylate or triacrylate, for example butanediol or ethylene glycol diacrylate or methacrylate and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. The process of the present invention can further utilize hydrogels which are prepared using polyallyl ethers as a crosslinker and by acidic homopolymerization of acrylic acid. Suitable crosslinkers are pentaerythritol triallyl and tetraallyl ethers, polyethylene glycol diallyl ether, ethylene glycol diallyl ether, glycerol diallyl ether, glycerol triallyl ether, polyallyl ethers based on sorbitol, and also ethoxylated variants thereof.

The preferred methods of making the base polymer which can be used in the process of the present invention are described in "Modern Superabsorbent Polymer Technology", F. L. Buchholz and A. T. Graham, Wiley-VCH, 1998, pages 77 to 84. Particular preference is given to base polymers which are prepared in a kneader, as described for example in WO-A-01/38402, or on a belt reactor, as described for example in EP-A-0 955 086.

The water-absbrbing polymer is preferably a polymeric acrylic acid or a polyacrylate. This water-absorbing polymer can be prepared by a process known from the literature. Preference is given to polymers which comprise crosslinking comonomers in amounts from 0.001 to 10 mol % and preferably 0.01 to 1 mol %, but very particular preference is given to polymers which were obtained by free-radical polymerization and where a polyfunctional ethylenically unsaturated free-radical crosslinker was used which additionally bears at least one free hydroxyl group (such as for example pentaerythritol triallyl ether or trimethylolpropane diallyl ether).

The swellable hydrogel-forming polymers are preparable by addition polymerization processes known per se. Preference is given to addition polymerization in aqueous solution conducted as a gel polymerization. It involves for example 15% to 50% by weight aqueous solutions of one or more hydrophilic monomers and if appropriate of a suitable grafting base being addition polymerized in the presence of a free-radical initiator by utilizing the Trommsdorff-Norrish effect (Makromol. Chem. 1, 169 (1947)), preferably without mechanical mixing. The addition polymerization reaction may be carried out in the temperature range between 0 and 150° C. and preferably between 10 and 100° C., not only at atmospheric pressure but also at superatmospheric or reduced pressure. As usual, the addition polymerization can also be carried out in a protective gas atmosphere, preferably under nitrogen. The addition polymerization may be induced using high-energy electromagnetic rays or the customary chemical addition polymerization initiators, for example organic peroxides, such as benzoyl peroxide, tert-butyl hydroperoxide, methyl ethyl ketone peroxide, cumene hydroperoxide, azo compounds such as azodiisobutyronitrile and also inorganic peroxo compounds such as $(NH_4)_2S_2O_8$ or $K_2S_2O_8$ or $H_2O_2$. They may be used if appropriate in combination with reducing agents such as sodium hydrogensulfite and iron(II) sulfate or redox systems, where the reducing component included is an aliphatic and aromatic sulfinic acid, such as benzenesulfinic acid and toluenesulfinic acid or derivatives of these acids, such as Mannich adducts of sulfinic acids, aldehydes and amino compounds, as described in DE-A-13 01 566. The performance characteristics of the polymers can be further improved by postheating the polymer gels in the temperature range from 50 to 130° C. and preferably from 70 to 100° C. for several hours.

The gels obtained are neutralized for example to 0 to 100 mol % preferably 5 to 90 mol % especially between 25 and 80 mol %, very preferably between 30 and 55 mol % and between 70 and 75 mol %, based on monomer used, for which the customary neutralizing agents can be used, preferably alkali metal hydroxides or alkali metal oxides, but more preferably sodium hydroxide, sodium carbonate and sodium bicarbonate.

Neutralization, is typically achieved by mixing the neutralizing agent as an aqueous solution or else preferably as a solid into the gel. For this, the gel is mechanically comminuted, for example by means of a meat grinder, and the neutralizing agent is sprayed on, scattered on or poured on and then carefully mixed in. The gel mass obtained can then be repeatedly passed through the meat grinder for homogenization. The neutralized gel mass is then dried with a belt or can dryer until the residual moisture content is preferably below 10% by weight and especially below 5% by weight. The dried hydrogel is subsequently ground and sieved, and the grinding can typically be carried out using roll mills, pin mills or swing mills. The particle size of the sieved hydrogel is preferably in the range from 45 to 1000 µm, more preferably in the range from 45 to 850 µm, even more preferably in the range from 100 to 800 µm and yet more preferably in the range from 100 to 700 µm. Further preferred particle sizes are in the range of 100-500 µm, 300-600 µm, smaller than 400 µm, more preferably smaller than 300 µm and most preferably smaller than 150 µm. At least 80%, and preferably at least 90% of all particles, come within these ranges.

The postcrosslinking of swellable hydrogel-forming polymers is typically carried out by spraying a solution of the surface postcrosslinker onto the dry base polymer powder.

After spraying, the polymeric powder is thermally dried, and the crosslinking reaction can take place not only before but also during the drying.

The spraying with a solution of the crosslinker is preferably carried out in reaction mixers or mixing and drying ranges, such as for example Lödige® mixers, BEPEX® mixers, NAUTA® mixers, SCHUGGI® mixers, NARA® dryers and PROCESSALL®. Fluidized bed dryers can be used as well.

Drying may take place in the mixer itself, by heating the jacket or introducing a stream of warm air. It is similarly possible to use a downstream dryer, such as for example a tray dryer, a rotary tube oven or a heatable screw. But it is also possible for example to utilize an azeotropic distillation as a drying process.

Preferred drying temperatures are in the range from 50 to 250° C., preferably in the range from 60 to 200° C. and more preferably in the range from 70 to 180° C. The preferred residence time at this temperature in the reaction mixer or dryer is below 60 minutes preferably below 30 minutes and more preferably below 10 minutes.

The surface postcrosslinkers can be used alone or combined with other surface postcrosslinkers, for example ethylene glycol diglycidyl ether, diethylene glycol diglycidyl ether, polyethylene glycol diglycidyl ether, propylene glycol diglycidyl ether, dipropylene glycol diglycidyl ether, polypropylene glycol diglycidyl ether, glycerol diglycidyl ether, polyglycerol diglycidyl ether, epichlorohydrin, ethylenediamine, ethylene glycol, diethylene glycol, triethylene glycol, polyethylene glycol, propylene glycol, dipropylene glycol, tripropylene glycol, polypropylene glycol, butylene glycol, 1,3-propanediol, 1,4-butanediol, bisphenol A, glycerol, trimethylolpropane, pentaerythritol, sorbitol, diethanolamine, triethanolamine, ethylenediamine, ethylene carbonate, propylene carbonate, 2-oxazolidones, such as 2-oxazolidinone or N-hydroxyethyl-2-oxazolidinone, 2,3-morpholinediones, such as N-2-hydroxyethyl-2,3-morpholindione, N-methyl-2,3-morpholindione, N-ethyl-2,3-morpholindione and/or N-tert-butyl-2,3-morpholindione, 2-oxotetrahydro-1,3-oxazine, N-acyl-2-oxazolidones, such as N-acetyl-2-oxazolidone, bicyclic amide acetals, such as 5-methyl-1-aza-4,6-dioxabicyclo[3.3.0]octane, 1-aza-4,6-dioxabicyclo[3.3.0]octane and/or 5-isopropyl-1-aza-4,6-dioxabicyclo[3.3.0]octane, and/or bis- and poly-2-oxazolidinones.

The surface postcrosslinker is preferably dissolved in solvents which are not self-reactive, preferably in lower alcohols, such as for example methanol, ethanol, isopropanol, propylene glycol, ethylene glycol, preferably isopropanol, most preferably in aqueous solutions of such suitable alcohols, in which case the alcohol content of the solution is in the range from 10% to 90% by weight, more preferably between 25% to 70% by weight and especially between 30% to 50% by weight.

The surface postcrosslinker is used in an amount from 0.01% to 1% by weight, based on the polymer used, and the crosslinker solution itself is used in an amount from 1% to 20% by weight and preferably from 3% to 15% by weight, based on the polymer used.

The AUL 0.7 psi value [g/g] of the swellable hydrogel-forming polymers of the present invention can be measured by the method reported in DE-A-199 09 653 and is preferably greater than 10, especially greater than 15, more preferably greater than 20, especially greater than 25 and especially preferably greater than 30.

The swellable hydrogel-forming polymers of the present invention are useful for absorbing blood and/or body fluids in hygiene articles, such as for example incontinence articles, napkins, tampons, liners. To this end, the swellable hydrogel-forming polymers of the present invention can be processed with fibers, such as cellulose for example, and also fibrous webs to form absorbing composites.

The dendritic polymers used in the process of the present invention are hydrophilic by virtue of their nonlinear structure, but their specific geometry substantially curtails any unwanted tendency for thermal postcrosslinking, so that the dendritic polymers can be added during the surface-postcrosslinking operation. There is no need for any additional admixing step. The globular shape is particularly advantageous here with regard to the viscosity of the aqueous solution in incipiently or fully swollen superabsorbents. Consequently, saline flow conductivity remains high, even at a high polymer use level.

The dustbinding ability of the dendritic polymer is excellent, especially the binding ability of dusty or powdery additives. There is virtually no detectable fine dust in the product after harsh mechanical exposure as well as directly after application.

The conveying properties of the end product are also influenced by the solvent used at surface postcrosslinking. Propylene glycol/water has distinct advantages over isopropanol/water. On the other hand, unconverted propylene glycol (unlike unconverted isopropanol) is difficult to remove and remains in the end product. The alcohol content of the dried end product is typically in the range from 5000 to 15 000 weight ppm when propylene glycol is used, but is less than 1000 weight ppm, preferably less than 500 weight ppm and more preferably less than 100 weight ppm when isopropanol is used, which is preferred.

The addition of dendritic polymers in the process of the present invention makes it possible to use isopropanol/water (30% by weight of isopropanol in water) as a solvent in surface postcrosslinking to obtain superabsorbents having conveying properties which were hitherto only available on using propylene glycol/water (30% by weight of propylene glycol in water).

To determine the quality of the present invention's aftertreatment, the dried hydrogel is tested by test methods described hereinbelow:

Methods:

The measurements should be carried out at ambient temperature of 23±2° C. and a relative humidity of 50±10%, unless otherwise stated. The swellable hydrogel-forming polymer is thoroughly mixed through for the measurement.

Centrifuge Retention Capacity (CRC)

This method measures the free swellability of the hydrogel in a teabag. 0.2000±0.0050 g of dried hydrogel (particle fraction 106-850 µm) are weighed in a teabag 60×85 mm in size, which is subsequently filled. The teabag is placed for 30 minutes in an excess of 0.9% by weight sodium chloride solution (at least 0.83 l of sodium chloride solution/1 g of polymer powder). The teabag is subsequently centrifuged at 250 G for 3 minutes. The amount of liquid retained by the hydrogel is determined by weighing back the centrifuged teabag.

Centrifuge retention capacity can also be determined by the centrifuge retention capacity test method No. 441.2-02 recommended by EDANA (European Disposables and Nonwovens Association).

Absorbency Under Load (AUL) 0.7 psi (4830 Pa)

The measuring cell for determining the AUL 0.7 psi value is a Plexiglas cylinder 60 mm in internal diameter and 50 mm in height. Adhesively attached to its underside is a stainless steel sieve bottom having a mesh size of 36 µm. The measuring cell further includes a plastic plate having a diameter of 59 mm and a weight which can be placed in the measuring cell together with the plastic plate. The plastic plate and the weight together weigh 1344 g. AUL 0.7 psi is determined by determining the weight of the empty Plexiglas cylinder and of the plastic plate and recording it as $W_0$. Then 0.900±0.005 g of swellable hydrogel-forming polymer (particle size distribution 150-800 µm) is weighed into the Plexiglas cylinder and distributed very uniformly over the stainless steel sieve bottom. The plastic plate is then carefully placed in the Plexiglas cylinder, the entire unit is weighed and the weight is recorded as $W_a$. The weight is then placed on the plastic plate in the Plexiglas cylinder. A ceramic filter plate 120 mm in diameter and 10 mm in height (Duran, from Schoft) and 0 in porosity is then placed in the middle of a Petri dish 200 mm in diameter and 30 mm in height and sufficient 0.9% by weight sodium chloride solution is introduced for the surface of the liquid to be level with the filter plate surface without the surface of the filter plate being wetted. A round filter paper 90 mm in diameter and <20 µm in pore size (S&S 589 Schwarzband from Schleicher & Schüll) is subsequently placed on the ceramic plate. The Plexiglas cylinder holding soluble hydrogel-forming polymer is then placed with plastic plate and weight on top of the filter paper and left there for 60 minutes. At the end of this period, the complete unit is taken out of the Petri dish from the filter paper and then the weight is removed from the Plexiglas cylinder. The Plexiglas cylinder holding swollen hydrogel is weighed out together with the plastic plate and the weight is recorded as $W_b$.

Absorbency under load (AUL) is calculated as follows:

$$AUL\ 0.7\ psi\ [g/g]=[W_b-W_a]/[W_a-W_0]$$

The absorbency under load can also be determined by the absoption under pressure test method No. 442.2-02 recommended by EDANA (European Disposables and Nonwovens Association).

Saline Flow Conductivity (SFC)

The saline flow conductivity of a swollen gel layer under a confining pressure of 0.3 psi (2070 Pa) is determined as described in EP-A-0 640 330 as the gel layer permeability of a swollen gel layer of superabsorbent polymer, although the apparatus described on page 19 and in FIG. 8 of the previously cited patent application was modified to the effect that the glass frit (40) is no longer used, the piston (39) is made of the same plastic material as the cylinder (37) and now contains 21 equally sized holes uniformly distributed over the entire contact surface. The procedure and also evaluation of the measurement remains unchanged compared with EP-A-0 640 330. The flow rate is recorded automatically.

The saline flow conductivity (SFC) is calculated as follows:

$$SFC\ [cm^3 s/g]=(F_g(t=0) \times L_0)/(d \times A \times WP),$$

where $F_g(t=0)$ is the flow rate of NaCl solution in g/s obtained from a linear regression analysis of the $F_g(t)$ data of the flow rate determinations by extrapolation to $t=0$; $L_0$ is the thickness of the gel layer in cm; d is the density of the NaCl solution in $g/cm^3$; A is the area of the gel layer in $cm^2$; and WP is the hydrostatic pressure above the gel layer in $dyn/cm^2$.

Flow Rate (FLR)

This method determines the rate at which the swellable hydrogel-forming polymer flows through a funnel. 100±0.01 of dried hydrogel are weighed into a sealable metal funnel. The weight of the swellable hydrogel-forming polymer is recorded as $W_1$. The funnel corresponds to German Industrial Specification DIN 53492. The efflux pipe of the funnel is 145.0±0.5 mm in height and 10.00±0.01 mm in internal diameter. The angle of inclination of the funnel's wall relative to the horizontal is 20°. The metal funnel is grounded. The funnel is subsequently opened and the time taken for the funnel to empty. The time is noted as t.

The measurement is carried out twice. The difference between the two measured values obtained must not be more than 5%.

The flow rate (FLR) is calculated as follows:

$$FLR\ [g/s]=W_1/t$$

The flow rate can also be determined by the flowrate test method No. 450.2-02 recommended by EDANA (European Disposables and Nonwovens Association).

Pour-out Weight (ASG)

This method determines the density of the swellable hydrogel-forming polymer after pouring out. The measurement is carried out with a cylindrical pycnometer conforming to DIN 53466. The pycnometer has a volume (V) of 100.0±0.5 ml, an internal diameter of 45.0±0.1 mm and a height of 63.1±0.1 mm. The pycnometer is weighed empty. The weight is noted as $W_1$. About 100 g of dried hydrogel are weighed into a sealable metal funnel. The weight is recorded as $W_1$. The funnel corresponds to German Industrial Specification DIN 53492. The efflux pipe of the funnel is 145.0±0.5 mm in height and 10.00±0.01 mm in internal diameter. The angle of inclination of the funnel's wall relative to the horizontal is 20°. The metal funnel and the pycnometer are grounded. The funnel is subsequently emptied into the pycometer, with excess swellable hydrogel-forming polymer overflowing.

The overflown swellable hydrogel-forming polymer is scraped off by means of a spatula. The filled pycnometer is weighed and the weight recorded as $W_2$.

The measurement is carried out twice. The difference between the two measured values obtained must not be more than 5%.

The pour-out weight (ASG) is calculated as follows:

$$ASG[g/ml]=[W_2-W_1]/V$$

The pour-out weight can also be determined by the density test method No. 460.2-02 recommended by EDANA (European Disposables and Nonwovens Association).

Fragility Test

The fragility test is used to determine the behavior of the swellable hydrogel-forming polymer when exposed to a mechanical stressor. The test is carried out with a sealable stoneware cup. The stoneware cup is 85.7 mm (3 ⅜ inches) in diameter, 111.1 mm (4 ⅜ inches) in height and 379 cm³ (0.1 gallons) in volume. The opening is 31.8 mm (1 ¼ inches) in diameter. The height with lid is 139.7 mm (5 ½ inches). The stoneware cup is filled with 50 g of swellable hydrogel-forming polymer and 127 g of cylindrical stoneware grinding media. The stoneware grinding media are 12.7 mm (½ inch) in diameter, 12.7 mm (½ inch) in height and about 5.3 g in individual weight. The stoneware cup is filled and rotated for 15 minutes on a rollmill (for example from U.S. Stoneware, US) at 180 rpm.

Dust

Dust fractions can be determined by the dust test method No.490.2-02 recommended by EDANA (European Disposables and Nonwovens Association).

Anticaking Test

A 100 ml glass beaker has 30 g of swellable hydrogel-forming polymer weighed into it. The beaker is subsequently stored at 40° C. and a relative humidity of 95% for 2 hours. After storage, the swellable hydrogel-forming polymer is poured out. The pour-out behavior is qualitatively assessed on a scale where "very poor" means that a stable skin has formed on the surface of the swellable hydrogel-forming polymer and the swellable hydrogel-forming polymer stays in the beaker, "very good" means that the swellable hydrogel-forming polymer can be fully poured out, and the values inbetween mean that a ring of swellable hydrogel-forming polymer remains on the walls of the beaker.

EXAMPLES

Examples 1 and 2

ASAP 500 Z base polymer was postcrosslinked in a Lödige laboratory mixer by spraying with 3.16% by weight of iso-propanol/water (30:70) and 0.085% by weight of 2-oxazolidinone, both percentages being based on the base polymer, and subsequent heating to 175° C. for 120 minutes. Dendritic polymers were added in the process as appropriate. The polymer obtained was subsequently sieved off at 850 μm and declumped. The products were tested and analyzed by laser falling tube method for fine dust (<10 μm). The same products were mechanically degraded by means of a roll mill and retested for dust.

TABLE 1

| Run | Additive | CRC [g/] | AUL 0.7 [g/g] | SFC [$10^7$ cm³s/g] | FLR [g/s] | ASG [g/ml] | Dust before mill [ppm] | Dust after mill [ppm] | Anticaking test |
|---|---|---|---|---|---|---|---|---|---|
| 1 | | 30.9 | 23.3 | 45 | 10.4 | 0.68 | 2 | 26 | very poor |
| 2 | 0.5 wt % of Boltorn ® H40 | 29.7 | 22.3 | 33 | 9.4 | 0.64 | 1 | <10 | n.d. |

The invention claimed is:

1. Swellable hydrogel-forming polymer particles comprising (a) a swellable hydrogel-forming polymer and (b) up to 10% by weight, based on the swellable hydrogel-forming polymer particles, of at least one hydrophilic polymer having a dendritic structure, wherein the swellable hydrogel-forming polymer particles have a particle size in the range of 45 to 1000 μm.

2. The polymer particles of claim 1 wherein said swellable hydrogel-forming polymer particles comprise at least 0.005%, by weight, of the hydrophilic polymer having a dendritic structure.

3. The polymer particles of claim 1 wherein the hydrophilic polymer having a dendritic structure comprises a polyester formed from a polyol and 2,2-dimethylolpropionic acid.

4. The polymer particles of claim 1 wherein the hydrophilic polymer having a dendritic structure comprises a polypropyleneimine, a polyamidoamine, or a polyesteramide.

5. The polymer particles of claim 1 further comprising a powdery additive, a dusty additive, or a mixture thereof.

6. The polymer particles of claim 5 wherein said additive is a metal salt, a pyrogenic silica, a polysaccharide, a nonionic surfactant, a wax, diatomaceous earth, or a mixture thereof.

7. The polymer particles of claim 5 wherein said additive is in a form of hollow microspheres from 1 to 1000 μm in diameter and having a wall thickness of 1% to 10% of said diameter.

8. The polymer particles of claim 1 comprising less than 50 weight ppm of particles less than 10 μm in diameter.

9. The polymer particles of claim 1 comprising less than 50 weight ppm of particles less than 10 μm in diameter after exposure to mechanical stress.

10. The polymer particles of claim 1 wherein the hydrophilic polymer having a dendritic structure is present on the surfaces of the swellable hydrogel-forming polymer particles.

11. The polymer particles of claim 1 wherein the swellable hydrogel-forming polymer particles comprise crosslinked, partially neutralized polyacrylic acid.

12. A process for preparing swellable hydrogel-forming polymer particles of claim 1 comprising mixing dried, water-absorbing hydrogel particles with at least one hydrophilic polymer having a dendritic structure.

13. The process of claim 12 wherein said hydrophilic polymer of dendritic structure comprises a polyester formed from a polyol and 2,2-dimethylolpropionic acid.

14. The process of claim 12 wherein said hydrophilic polymer of dendritic structure comprises a polypropyleneimine, a polyamidoamine, or a polyesteramide.

15. The process of claim 12 further comprising a surface-postcrosslinking operation.

16. The process of claim 15 wherein the surface-postcrosslinking operation is performed using at least one surface postcrosslinker and a solvent comprising a mixture of isopropanol and water.

17. A method of absorbing blood or body fluids comprising contacting the blood or body fluids with the swellable hydrogel-forming polymer particles of claim 1.

18. The method of claim 17 wherein the body fluid is urine.

19. A hygiene article comprising the swellable hydrogel-forming polymer particles of claim 1, said articles selected from the group consisting of diapers, incontinence articles, sanitary napkins, tampons, and liners.

* * * * *